(12) United States Patent
Wan et al.

(10) Patent No.: US 10,384,205 B2
(45) Date of Patent: Aug. 20, 2019

(54) INTEGRATED SAMPLING AND DETECTION DEVICE WITH MISASSEMBLY PREVENTION STRUCTURE

(71) Applicant: W.H.P.M. BIORESEARCH AND TECHNOLOGY CO., LTD., Beijing (CN)

(72) Inventors: John Wan, Beijing (CN); Qinghai Xia, Beijing (CN); Panpan Hou, Beijing (CN); Jie Liu, Beijing (CN)

(73) Assignee: W.H.P.M. BIORESEARCH AND TECHNOLOGY CO., LTD., Beijing (CN)

( * ) Notice: Subject to any disclaimer, the term of this patent is extended or adjusted under 35 U.S.C. 154(b) by 265 days.

(21) Appl. No.: 15/321,330

(22) PCT Filed: May 19, 2016

(86) PCT No.: PCT/CN2016/082666
§ 371 (c)(1),
(2) Date: Dec. 22, 2016

(87) PCT Pub. No.: WO2016/188362
PCT Pub. Date: Dec. 1, 2016

(65) Prior Publication Data
US 2017/0189900 A1    Jul. 6, 2017

(30) Foreign Application Priority Data
May 28, 2015    (CN) .......................... 2015 1 0284103

(51) Int. Cl.
*G01N 21/75*   (2006.01)
*B01L 3/00*    (2006.01)
(Continued)

(52) U.S. Cl.
CPC .......... *B01L 3/508* (2013.01); *A61B 10/0038* (2013.01); *B01L 3/502* (2013.01);
(Continued)

(58) Field of Classification Search
CPC .. B01L 3/508; B01L 3/502; B01L 2300/0663; B01L 2300/046;
(Continued)

(56) References Cited

U.S. PATENT DOCUMENTS

2004/0133128 A1    7/2004   Guan et al.
2005/0142040 A1    6/2005   Hanawa et al.
(Continued)

FOREIGN PATENT DOCUMENTS

CN    1624485 A    6/2005
CN    2725894 Y    9/2005
(Continued)

OTHER PUBLICATIONS

International Search Report dated Aug. 24, 2016 issued in PCT/CN2016/082666.
(Continued)

*Primary Examiner* — Dennis White
(74) *Attorney, Agent, or Firm* — Scully, Scott, Murphy & Presser, P.C.

(57) ABSTRACT

The invention provides a collection and detection integrated device with a mis-assembling prevention structure. The collection and detection integrated device with a mis-assembling prevention structure comprises: a detector; a test strip holder, detachably arranged in the detector; a collector, detachably contained in the detector; a faeces collection piece and a cushion block, configured to detachably seal the collector; and a piercing part, arranged on a bottom surface of the detector and configured to pierce the collector, wherein the test strip holder and the collector are contained
(Continued)

in the detector side by side, the collector is located between the test strip holder and the detector, a first outer side face of the collector is adjacent to an inner side wall of the detector, a second outer side face of the collector is adjacent to the test strip holder, and the first outer side face and the second outer side face of the collector are asymmetric structurally. The invention solves the problem that a side, bonded with a bar code, of a collector is mis-assembled into a side, close to a test strip holder, of a detector, and also avoids a phenomenon of mis-bonding of a bar code.

15 Claims, 21 Drawing Sheets

(51) Int. Cl.
 *G01N 1/08* (2006.01)
 *G01N 33/543* (2006.01)
 *A61B 10/00* (2006.01)

(52) U.S. Cl.
 CPC ......... *G01N 1/08* (2013.01); *G01N 33/54366* (2013.01); *B01L 2200/025* (2013.01); *B01L 2300/021* (2013.01); *B01L 2300/046* (2013.01); *B01L 2300/0609* (2013.01); *B01L 2300/0663* (2013.01); *B01L 2300/0672* (2013.01); *B01L 2300/0825* (2013.01); *B01L 2300/0858* (2013.01)

(58) Field of Classification Search
 CPC ..... B01L 2300/0609; B01L 2300/0672; B01L 2300/0825; B01L 2300/0858; B01L 2200/025; B01L 2300/021; A61B 10/0038; G01N 33/54366; G01N 1/08
 See application file for complete search history.

(56) References Cited

U.S. PATENT DOCUMENTS

| | | |
|---|---|---|
| 2006/0212021 A1 | 9/2006 | Yazaki et al. |
| 2006/0292035 A1* | 12/2006 | Gould ............... A61B 10/0051 |
| | | 422/417 |
| 2009/0031790 A1 | 2/2009 | Guo et al. |
| 2010/0294050 A1 | 11/2010 | Massaro |
| 2016/0051235 A1* | 2/2016 | Wan ................... A61B 10/0038 |
| | | 436/164 |

FOREIGN PATENT DOCUMENTS

| | | |
|---|---|---|
| CN | 1764413 A | 4/2006 |
| CN | 101351153 A | 1/2009 |
| CN | 201177580 Y | 1/2009 |
| CN | 201417273 Y | 3/2010 |
| CN | 201555723 U | 8/2010 |
| CN | 101876661 A | 11/2010 |
| CN | 102053149 A | 5/2011 |
| CN | 102564796 A | 7/2012 |
| CN | 102621295 A | 8/2012 |
| CN | 103217313 A | 7/2013 |
| CN | 203241258 U | 10/2013 |
| CN | 104849440 A | 8/2015 |
| CN | 204613211 U | 9/2015 |
| JP | 2008-191070 A | 8/2008 |
| WO | WO 2014/177927 A2 | 11/2014 |
| WO | WO 2014/190355 A1 | 11/2014 |
| WO | WO 2015/052901 A1 | 4/2015 |

OTHER PUBLICATIONS

Supplementary European Search Report dated EP 16 79 4199 dated Aug. 4, 2017.

* cited by examiner

INTEGRATED SAMPLING AND DETECTION DEVICE WITH MISASSEMBLY PREVENTION STRUCTURE

TECHNICAL FIELD OF THE INVENTION

The invention relates to the field of medical detections, specifically to a faeces collection and detection device, and particularly to a collection and detection integrated device with a mis-assembled prevention structure.

BACKGROUND OF THE INVENTION

After a collector of a faeces collection and detection device in the traditional art is bonded with a bar code, when the collector bonded with the bar code is assembled into a detector of the faeces collection and detection device, the side, bonded with the bar code, of the collector is easily mis-assembled into a side, close to a test strip holder, of the detector without correct attachment to the detector due to the fact that the collector is of a symmetric regular structure, thereby influencing reading of the bar code.

To sum up, the problem that a side, bonded with a bar code, of a collector is easily mis-assembled into a side, close to a test strip holder, of a detector exists in the traditional art.

SUMMARY OF THE INVENTION

The invention provides a collection and detection integrated device with a mis-assembling prevention structure, which is intended to solve the problem that a side, bonded with a bar code, of a collector is mis-assembled into a side, close to a test strip holder, of a detector.

To this end, the invention provides a collection and detection integrated device with a mis-assembling prevention structure. The collection and detection integrated device with a mis-assembling prevention structure may include: a detector; a test strip holder, provided in the detector detachably; a collector, accommodated in the detector detachably; a faeces collection piece and a cushion block, configured to seal the collector detachably; and a piercing part, provided on a bottom surface of the detector and configured to pierce the collector, wherein the test strip holder and the collector are accommodated in the detector side by side, the collector is located between the test strip holder and the detector, a first outer side face of the collector is adjacent to an inner side wall of the detector, a second outer side face of the collector is adjacent to the test strip holder, and the first outer side face and the second outer side face of the collector are asymmetric structurally.

Furthermore, the first outer side face of the collector is a plane, and the second outer side face of the collector is a curved surface.

Furthermore, the second outer side face of the collector is a convex arc-shaped surface.

Furthermore, a recess area may be arranged on the second outer side face of the collector, and the recess area is provided with a convex rib or a convex needle-shaped body or a convex column body of the collector.

Furthermore, the collection and detection integrated device with a mis-assembling prevention structure further comprises: a supporting platform provided at a bottom of the detector and configured to support the collector.

Furthermore, the piercing part is an annular body, a top surface of the annular body is a spiral surface, and the top surface of the annular body may be provided with a sharp corner.

Furthermore, the piercing part comprises: a pointed cone body and an annular frustum surrounding the pointed cone body, the pointed cone body is higher than the annular frustum, an annular clearance is provided between the pointed cone body and the annular frustum, a side surface of the annular frustum is provided with an opening, the opening faces the test strip holder, and the annular clearance is communicated with the opening to form a liquid flow passage.

Furthermore, the annular body is provided with a taper for flow guide from top to bottom.

Furthermore, the piercing part comprises: a piercing needle and three prisms provided evenly around the piercing needle and connected with the piercing needle, the piercing needle is higher than the three prisms.

Furthermore, the annular body comprises two pairs of semi-rings, the two semi-rings of each pair are opposite to each other; the four semi-rings are provided side by side; and the piercing part further comprises: a T-shaped prism, an outer side of each of two peripheral semi-rings which are provided at the outer sides of the four semi-rings are connected with the T-shaped prism.

Furthermore, the side face of the test strip holder is provided with a slope decreasing from top to bottom, and an inner side of the detector may be provided with a convex rib, corresponding to the slope of the test strip holder, of the detector.

Furthermore, a trench is provided on an outer side of the test strip holder, a test strip is mounted on the trench, an inner wall of one side, adjacent to the test strip, of the detector is provided with a slope from top to bottom, three other inner walls of the detector are provided with slopes from the top to a detector critical line, a straight wall vertical to the bottom surface of the detector is provided below the detector critical line, and the detector critical line is provided on the inner wall of the detector and vertical to a length direction of the detector.

Furthermore, a test strip holder critical line is provided on an inner side of the test strip holder, the inner side of the test strip holder is provided with a slope from the top to the test strip holder critical line, and a straight wall vertical to the bottom surface of the detector is provided below the test strip holder critical line.

Furthermore, a die drawing direction of the collector is inward die drawing from bottom to top, a lower end of the collector is larger than an upper end of the collector, and a lower end of the detector is smaller than an upper end of the detector.

Furthermore, the annular body comprises two pairs of semi-rings, the two semi-rings of each pair are opposite to each other; the four semi-rings are provided side by side; and an outer side of each of two peripheral semi-rings which are provided at the outer sides of the four semi-rings are connected with a T-shaped prism.

Furthermore, a trench is provided on an outer side of the test strip holder, a test strip is mounted on the trench, an inner wall of one side, adjacent to the test strip, of the detector is provided with a slope from top to bottom, three other inner walls of the detector are provided with slopes from the top to a detector critical line, the three other inner walls, below the detector critical line, of the detector are straight walls vertical to the bottom surface of the detector, and the detector critical line is provided on the inner wall of the detector and vertical to a length direction of the detector.

Furthermore, a test strip holder critical line is provided on an inner side of the test strip holder, an inner wall of the test strip holder is provided with a slope from the top to the test strip holder critical line, and the inner wall, below the test strip holder critical line, of the test strip holder is a straight wall vertical to the bottom surface of the detector.

In the invention, two outer side faces of a collector are asymmetric structurally. Thus, a side face bonded with a bar code can be obviously distinguished from a side face facing a detector or attached to the detector.

Further, the side face, not bonded with a bar code, of the collector is set as a convex arc-shaped surface, a recess area is provided on the convex arc-shaped surface, and the recess area is provided with a convex rib or a convex needle-shaped body or a convex column body of the collector, such that it is very difficult to bond the side face, not bonded with a bar code, of the collector with a bar code, thereby avoiding a phenomenon of mis-bonding of a bar code.

Further, a die drawing direction of the collector is inward die drawing from bottom to top, and accordingly, a lower end of the collector is larger than an upper end of the collector while a lower end of the detector is smaller than an upper end of the detector. In conjunction with the circular arc shape of a test strip holder, a mis-assembling prevention effect can be achieved at the beginning of mounting, such that the problem that the side, bonded with the bar code, of the collector is mis-assembled into the side, close to the test strip holder, of the detector is fundamentally avoided, and correct mounting of the collector bonded with the bar code and normal reading of the bar code are achieved.

DRAWING MARK ILLUSTRATIONS 1, detector; 3, collector; 4, faeces collection piece; 5, cushion block; 6, aluminium foil; 7, test strip holder; 8, test strip; 9, transparent label;

31, first outer side face; 32, second outer side face; 10, bottom surface; 11, supporting platform; 15, annular body;

151, top surface; 152, opening; 111, convex rib; 113, detector critical line;
13, pointed cone body; 14, annular frustum; 142, opening;
16, annular body; 162, opening;
17, piercing needle; 18, prism;
19, T-shaped prism; 191, edge; 192, edge;
70, outer side of test strip holder; 71, trench; 72, inner wall; and 75, test strip holder critical line.

DETAILED DESCRIPTION OF THE EMBODIMENTS

In order to more clearly understand the technical features, purposes and effects of the invention, the invention will be illustrated with reference to the drawings.

Figure 1:
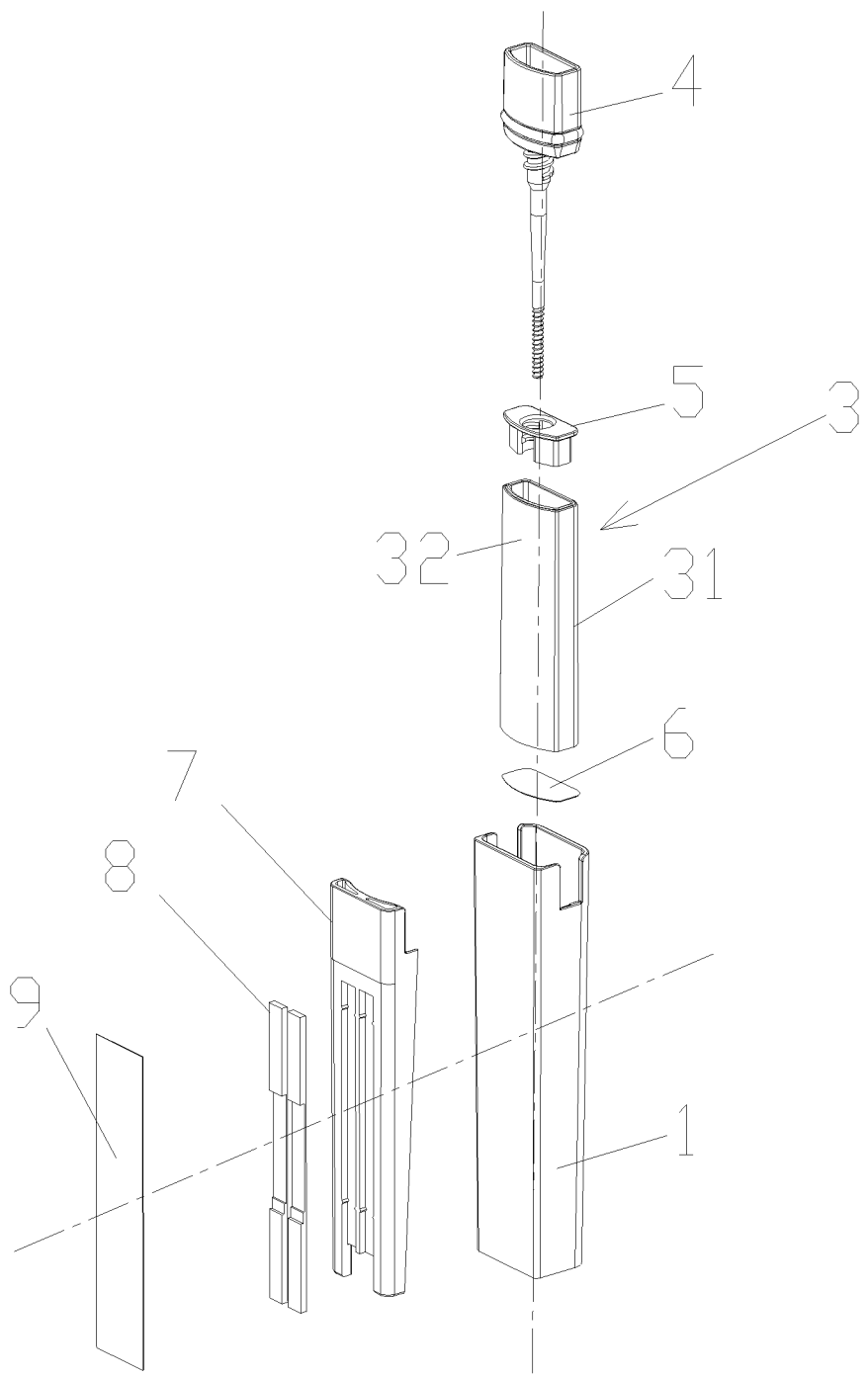
FIG. 1 is a three-dimensional breakdown structure diagram of a collection and detection integrated device with a mis-assembling prevention structure according to an embodiment of the invention.
Figure 2:
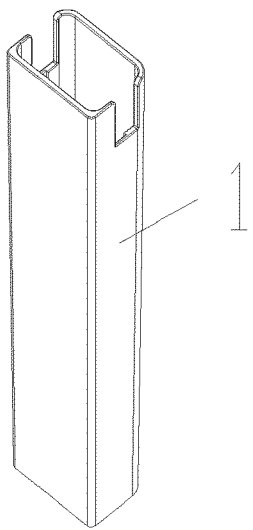
FIG. 2 is a three-dimensional structure diagram of a detector of a collection and detection integrated device with a mis-assembling prevention structure according to an embodiment of the invention.
Figure 3:
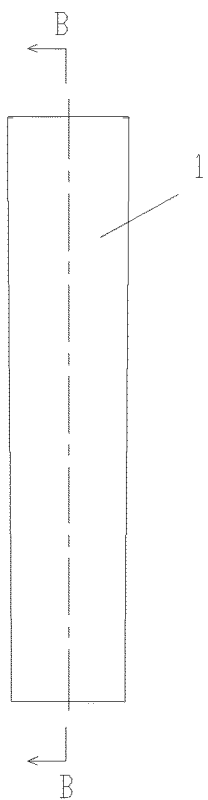
FIG. 3 is a front elevational view structure diagram of a detector according to an embodiment of the invention.
Figure 4:
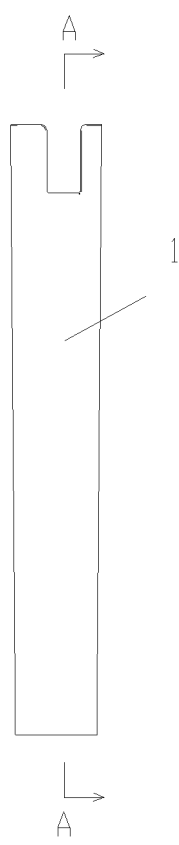
FIG. 4 is a side elevational view structure diagram of a detector according to an embodiment of the invention.

The invention provides a collection and detection integrated device with a mis-assembling prevention structure, which is also called as a faeces detection device. As shown in FIG. 1, the collection and detection integrated device with a mis-assembling prevention structure comprises: a detector 1 (as shown in FIG. 2, FIG. 3 and FIG. 4, the detector is barrel-shaped, for instance, square barrel-shaped, and is also called as a detection barrel, and a bottom is provided with a detector bottom surface 10); a test strip holder 7, provided in the detector 1 detachably; a collector 3, accommodated in the detector detachably; a faeces collection piece 4 and a cushion block 5, configured to seal the collector 3 detachably; and a piercing part (for instance, an annular body 15 with reference to FIG. 5), provided on a bottom surface 10 of the detector and configured to pierce the collector.

Figure 14:
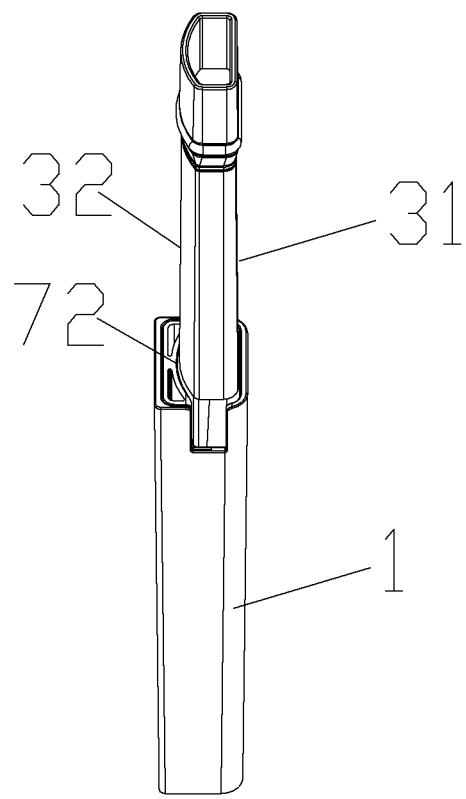
FIG. 14 is a mounting diagram of a faeces collection piece, a cushion block, a collector and a test strip holder according to an embodiment of the invention, wherein the faeces collection piece, the cushion block, the collector and the test strip holder are assembled into a detector in a forward direction.

Wherein, as shown in FIG. 14, FIG. 16, FIG. 17, FIG. 18 and FIG. 19, the test strip holder 7 and the collector 3 are accommodated in the detector 1 side by side, and the collector 3 is located between the test strip holder 7 and the detector 1. As shown in FIG. 1 and FIG. 14, a first outer side face 31 of the collector 3 is adjacent to an inner side wall of the detector 1, a second outer side face 32 of the collector is adjacent to the test strip holder 7, and the first outer side face 31 and the second outer side face 32 of the collector are asymmetric structurally. Thus, two side faces of the collector can be obviously distinguished, and which side face bonded with a bar code and which side face faced a detector or clung to the detector can be judged. So, the problem that a side, bonded with a bar code, of a collector is mis-assembled into a side, close to a test strip holder, of a detector is solved. In addition, the first outer side face 31 of the collector can be bonded with a text label of a bar code, thereby avoiding mis-bonding of the bar code. A recess area is provided on the second outer side face 32, not bonded with a bar code, of the collector 3, and the recess area is provided with a convex rib or a convex needle-shaped body or a convex column body of the collector, such that it is very difficult to bond the second outer side face 32, not bonded with a bar code, with a bar code, thereby avoiding a phenomenon of mis-bonding of a bar code.

In addition, once a side bonded with a bar code is mis-assembled into a side, close to a test strip holder, of a detector in the prior art, it is difficult to take out and reassemble the mis-assembled part due to the fact that the whole faeces collection and detection device has a compact structure, thereby scraping a set of faeces collection and detection device. Moreover, even if the collector can be taken out, the bar code thereon is probably abraded in assemble-in and take-out processes, and reading of the bar code will be influenced. The invention avoids the above problem.

In addition, as shown in FIG. 1, the collection and detection integrated device with a mis-assembling prevention structure may further comprise: the cushion block 5 in threaded connection with the faeces collection piece 4, an aluminium foil 6 packaged at a bottom of the collector 3, a test strip 8 mounted on the test strip holder 7, and a transparent label 9 covering the test strip 8. Other structures of the collection and detection integrated device with a mis-assembling prevention structure or relevant functions and structures not mentioned by the above parts may adopt a relevant technology in CN201320139144.6 or refer to descriptions in CN201320139144.6.

Figure 15:
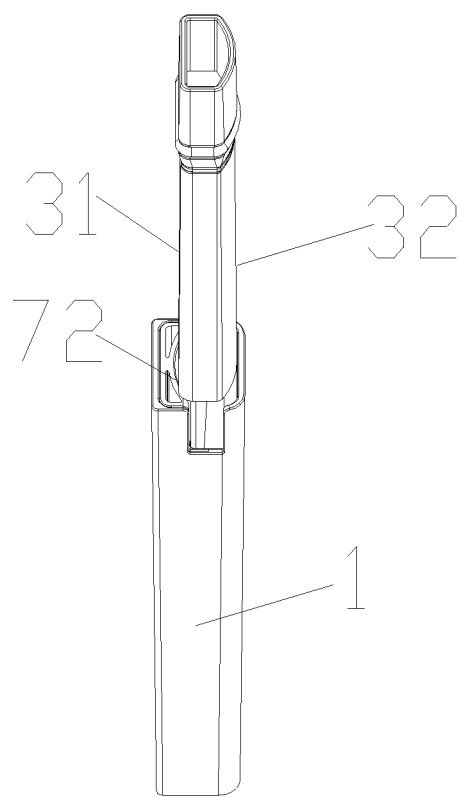
FIG. 15 is a mounting diagram of a faeces collection piece, a cushion block, a collector and a test strip holder according to an embodiment of the invention, wherein the faeces collection piece, the cushion block, the collector and the test strip holder are assembled into a detector in a reverse direction.

Furthermore, as shown in FIG. 1, FIG. 14 and FIG. 15, the first outer side face 31 of the collector is a plane configured to bond a bar code, and the second outer side face 32 of the collector is a curved surface configured to prevent or hinder bonding of the bar code and configured to fit the test strip holder. Thus, the device is convenient to manufacture, and the two side faces of the collector are easily distinguished.

Furthermore, as shown in FIG. 1, FIG. 14 and FIG. 15, the second outer side face 32 of the collector is a convex arc-shaped surface. For instance, the second outer side face 32 is circular arc-shaped. Thus, the bar code is not easily bonded thereon, and it is also convenient to fit the test strip holder.

Furthermore, a recess area is provided on the second outer side face 32 of the collector. For instance, a recess area is provided on the circular arc-shaped second outer side face 32, and the recess area is provided with a convex rib or a convex needle-shaped body or a convex column body of the collector. Thus, bonding of the bar code can be further prevented.

Figure 5:
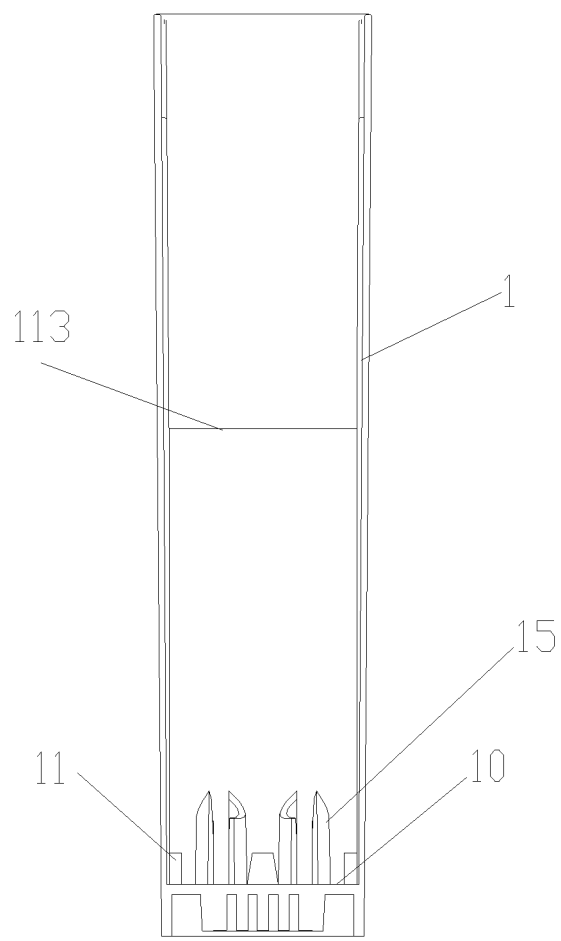
FIG. 5 is an A-A section view structure diagram of FIG. 4.
Figure 7:
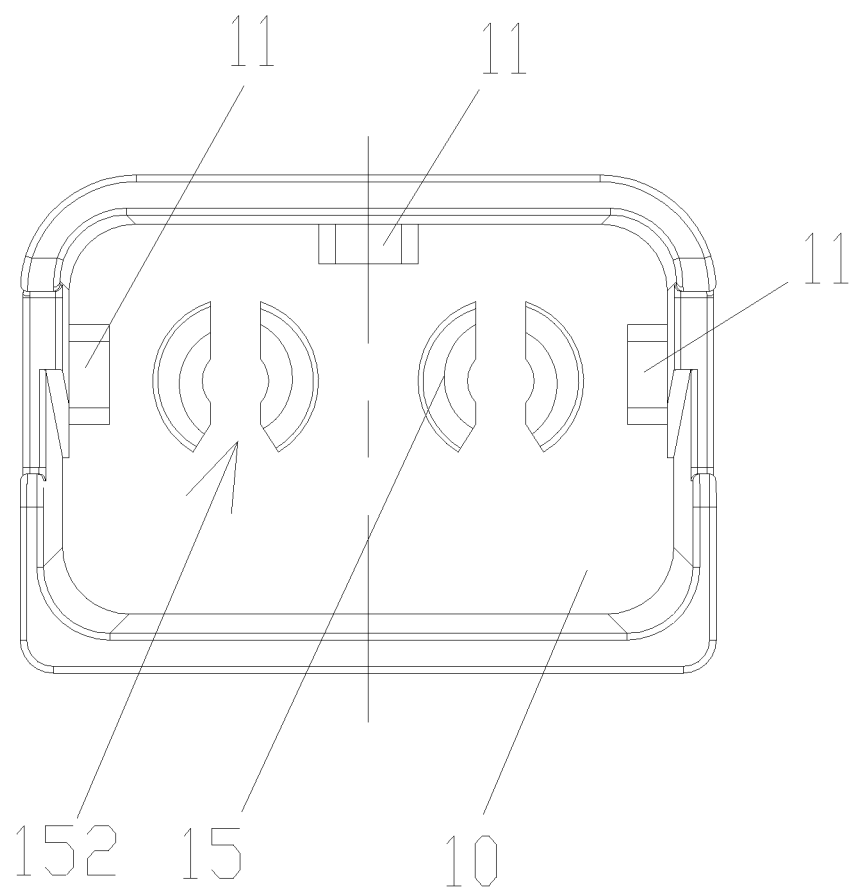
FIG. 7 is a top plan view structure diagram of a detector according to an embodiment of the invention.
Figure 8:
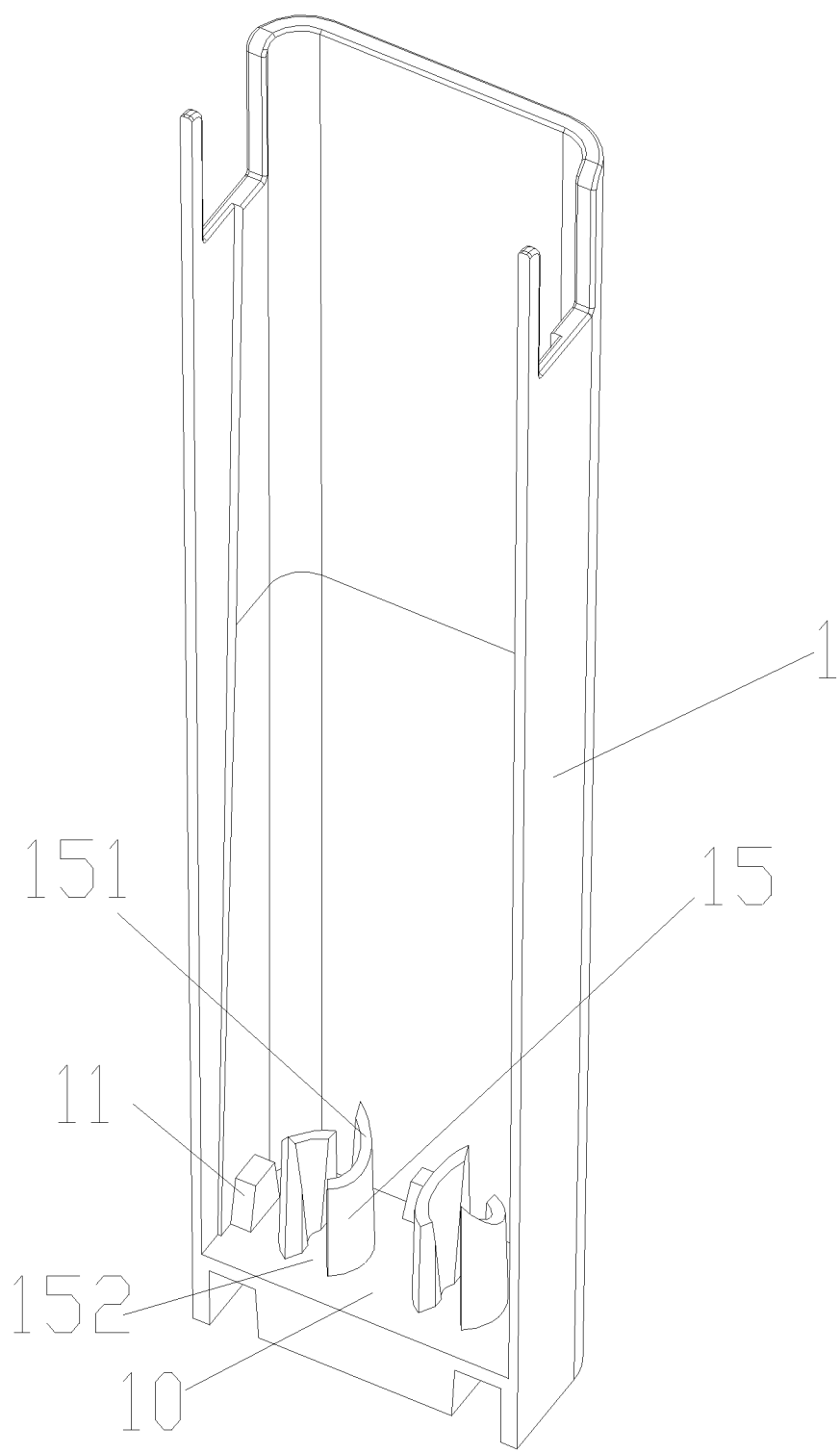
FIG. 8 is an internal three-dimensional structure diagram of a detector according to an embodiment of the invention.

Furthermore, as shown in FIG. 5, FIG. 7 and FIG. 8, the collection and detection integrated device with a mis-assembling prevention structure further comprises: a supporting platform 11 provided at a bottom of the detector and configured to support the collector. The supporting platform 11 is provided on the bottom surface 10 of the detector and protrudes from the bottom surface 10 of the detector, thereby ensuring a certain distance between the bottom of the collector and the bottom surface of the detector, and making it convenient for a diluent with a faeces sample to flow out.

Furthermore, FIG. 7 and FIG. 8 show a first piercing part, the piercing part is an annular body 15, a top surface 151 of the annular body is a spiral surface, and the top surface of the annular body is provided with a sharp corner. The annular body 15 comprises two pairs of semi-rings such as semi circular rings, the two semi-rings of each pair are opposite to each other; a pair of openings 152 is reserved in each pair of opposite semi circular rings; and two pairs of openings 152 are parallel to each other, in order that the diluent with the faeces sample flows out after the bottom of the collector is pierced.

Figure 20:
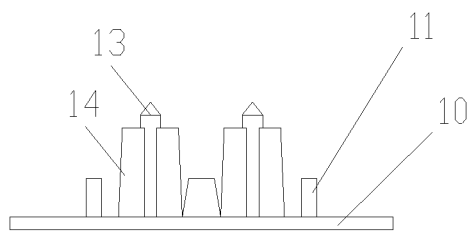
FIG. 20 is a front elevational view structure diagram of a piercing part with a pointed cone body and an annular frustum according to an embodiment of the invention.
Figure 21:
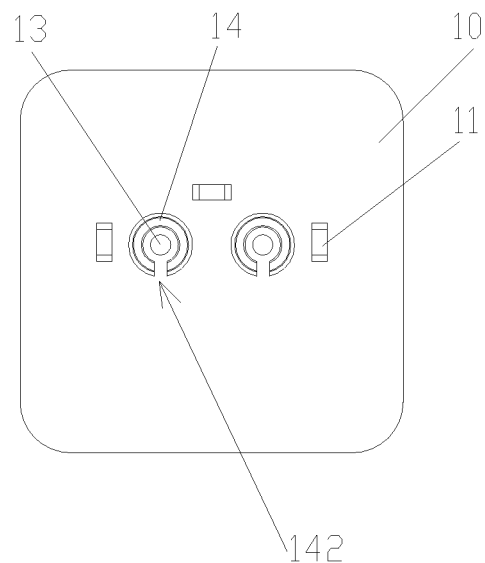
FIG. 21 is a top plan view structure diagram of a piercing part with a pointed cone body and an annular frustum according to an embodiment of the invention.
Figure 22:
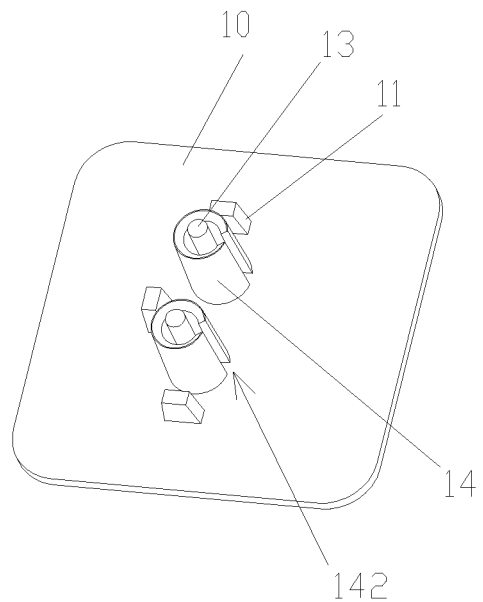
FIG. 22 is a three-dimensional structure diagram of a piercing part with a pointed cone body and an annular frustum according to an embodiment of the invention.

Furthermore, FIG. 20, FIG. 21 and FIG. 22 show a second piercing part, the piercing part comprises: a pointed cone body 13 and an annular frustum 14 surrounding the pointed cone body, the pointed cone body 13 is higher than the annular frustum 14, and the annular frustum 14 has a taper from top to bottom, thereby improving the probability of piercing. An annular clearance is provided between the pointed cone body and the annular frustum, a side surface of each annular frustum is provided with an opening 142, the opening faces the test strip holder, and the annular clearance is communicated with the opening 142 to form a liquid flow passage, thereby making it convenient for the diluent with the faeces sample to flow out. The second piercing part improves the probability of piercing and makes it convenient for the diluent with the faeces sample to flow out to the side of the test strip holder.

Figure 23:
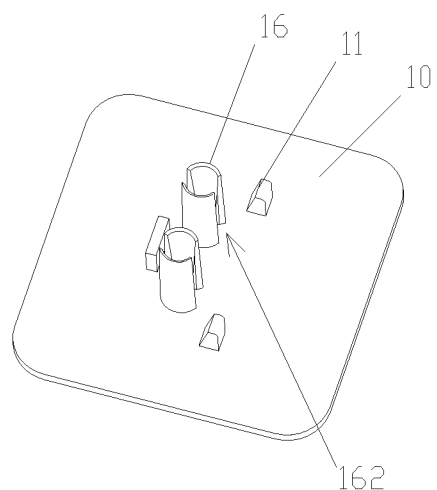
FIG. 23 is a three-dimensional structure diagram showing that a piercing part is an annular body with a flow guide taper according to an embodiment of the invention.
Figure 24:
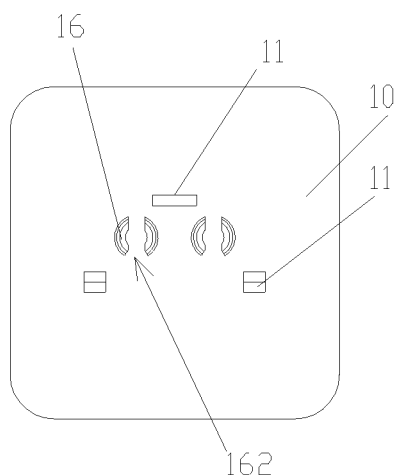
FIG. 24 is a top plan view structure diagram showing that a piercing part is an annular body with a flow guide taper according to an embodiment of the invention.
Figure 25:
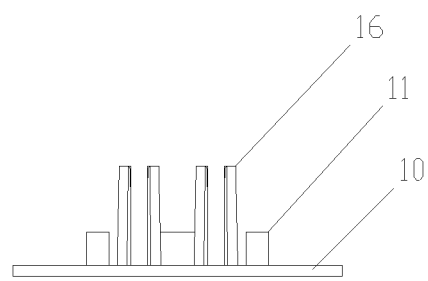
FIG. 25 is a front elevational view structure diagram showing that a piercing part is an annular body with a flow guide taper according to an embodiment of the invention.

Furthermore, FIG. 23, FIG. 24 and FIG. 25 show a third piercing part, and the third piercing part is improved on the basis of the first piercing part. The main improvement is embodied in that an annular body 16 (comprising inner and outer sides of the annular body 16) is provided with a taper for flow guide from top to bottom. In addition, the annular body 16 comprises two pairs of semi circular rings, the two semi circular rings of each pair are opposite to each other; a pair of openings 162 is reserved in each pair of opposite semi circular rings; and two pairs of openings 162 are parallel to each other, in order that the diluent with the faeces sample flows out after the bottom of the collector is pierced. Thus, compared with the first piercing part, the third piercing part can guide the diluent with the faeces sample to flow out.

Figure 26:
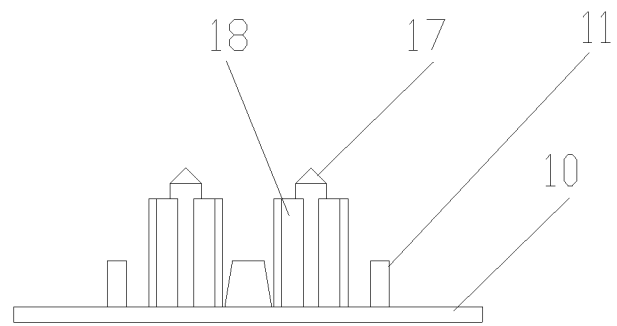
FIG. 26 is a front elevational view structure diagram showing that a piercing part is a piercing needle and three prisms according to an embodiment of the invention.
Figure 27:
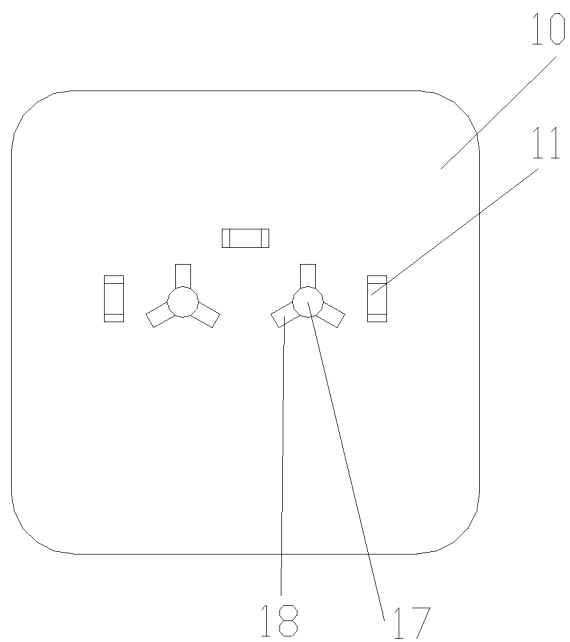
FIG. 27 is a top plan view structure diagram showing that a piercing part is a piercing needle and three prisms according to an embodiment of the invention.

Furthermore, FIG. 26 and FIG. 27 show a fourth piercing part, the piercing part comprises: a piercing needle 17 and three prisms 18 provided evenly around the piercing needle and connected with the piercing needle, each of the prisms 18 is a rectangular-shaped, the piercing needle 17 being higher than the three prisms 18. Thus, not only the piercing needle can pierce the bottom of the collector, but also the prisms 18 can pierce the bottom of the collector, thereby improving the probability of piercing.

Figure 28:
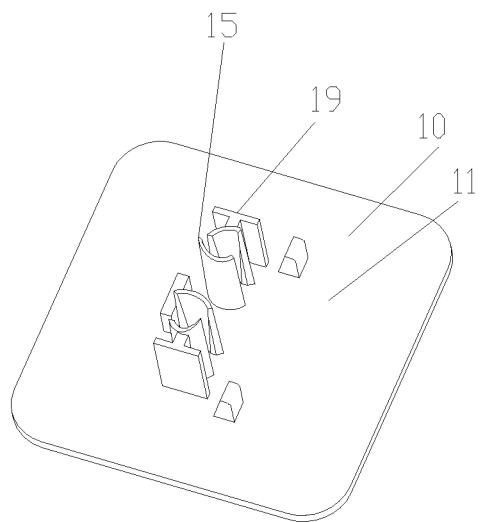
FIG. 28 is a three-dimensional structure diagram of a piercing part with a T-shaped prism according to an embodiment of the invention.
Figure 29:
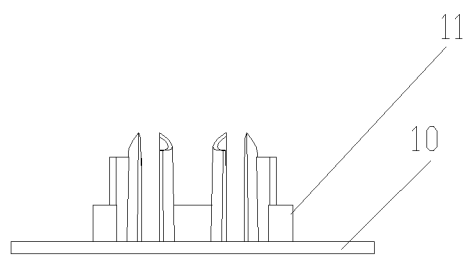
FIG. 29 is a front elevational view structure diagram of a piercing part with a T-shaped prism according to an embodiment of the invention.
Figure 30:
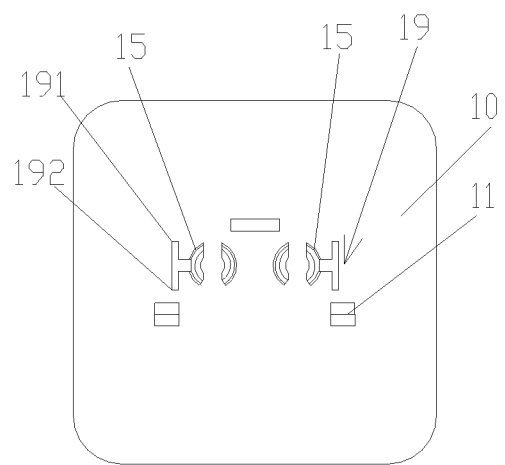
FIG. 30 is a top plan view structure diagram of a piercing part with a T-shaped prism according to an embodiment of the invention.

Furthermore, FIG. 28, FIG. 29 and FIG. 30 show a fifth piercing part, and the fifth piercing part is added with a T-shaped prism 19 on the basis of the first piercing part. The annular body 15 comprises four semi-rings divided into two pairs of semi-rings, the two semi-rings of each pair are opposite to each other; the four semi-rings are provided side by side; and an outer side of each of two peripheral semi-rings which are provided at the outer sides of the four semi-rings are connected with a T-shaped prism. The T-shaped prism 19 is provided with an edge 191 and an edge 192 configured to pierce the aluminium foil at the bottom of the collector, such that the probability of piercing is improved.

Figure 6:
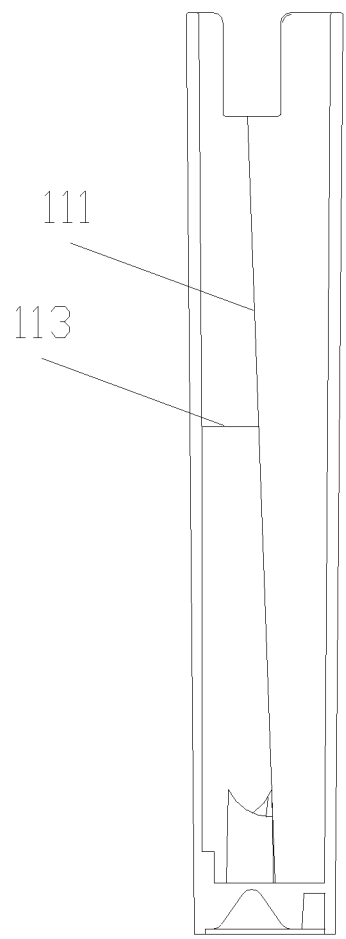
FIG. 6 is a B-B section view structure diagram of FIG. 3.

Furthermore, the side face of the test strip holder 7 is provided with a slope decreasing from top to bottom. In addition, as shown in FIG. 6, the inner side of the detector is provided with a convex rib 111, corresponding to the slope of the test strip holder, of the detector. The slope matches with the slope of the test strip holder, such that the test strip holder can be assembled into the detector and clung to the detector at the same time when the test strip holder is assembled into the detector, thereby making a fit part of the test strip holder and the detector self-sealed.

Figure 9:
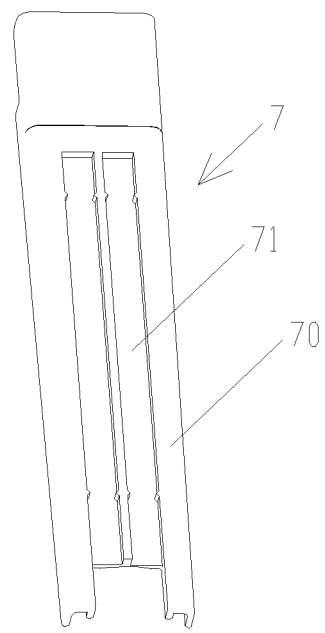
FIG. 9 shows a three-dimensional structure of a test strip holder according to an embodiment of the invention from a front elevational view direction.
Figure 11:
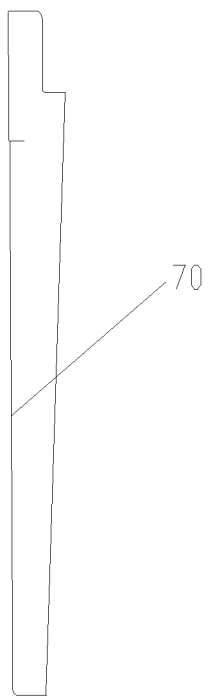
FIG. 11 is a side elevational view structure diagram of a test strip holder according to an embodiment of the invention.

Furthermore, as shown in FIG. 1, FIG. 9 and FIG. 11, a trench 71 is provided on an outer side 70 of the test strip holder, and a test strip 8 is mounted on the trench. As shown in FIG. 5 and FIG. 6, an inner wall of one side, adjacent to the test strip, of the detector is provided with a slope from top to bottom, the slope gradually decreases, three other inner walls of the detector are provided with slopes from the top to a detector critical line 113 (also called as an edge on the inner wall of the detector), the slope gradually decreases, a straight wall vertical to a bottom surface of the detector is provided below the detector critical line 113, and the detector critical line 113 is provided on an inner wall of the detector and vertical to a length direction of the detector 1. The detector critical line is provided on the side, close to the collector, of the detector, starts from a convex rib on one side of the detector and terminates to a convex rib on the other side of the detector. The detector critical line is located at a position, ⅓ to ½ of a height of the whole detector, below a top opening.

Figure 16:
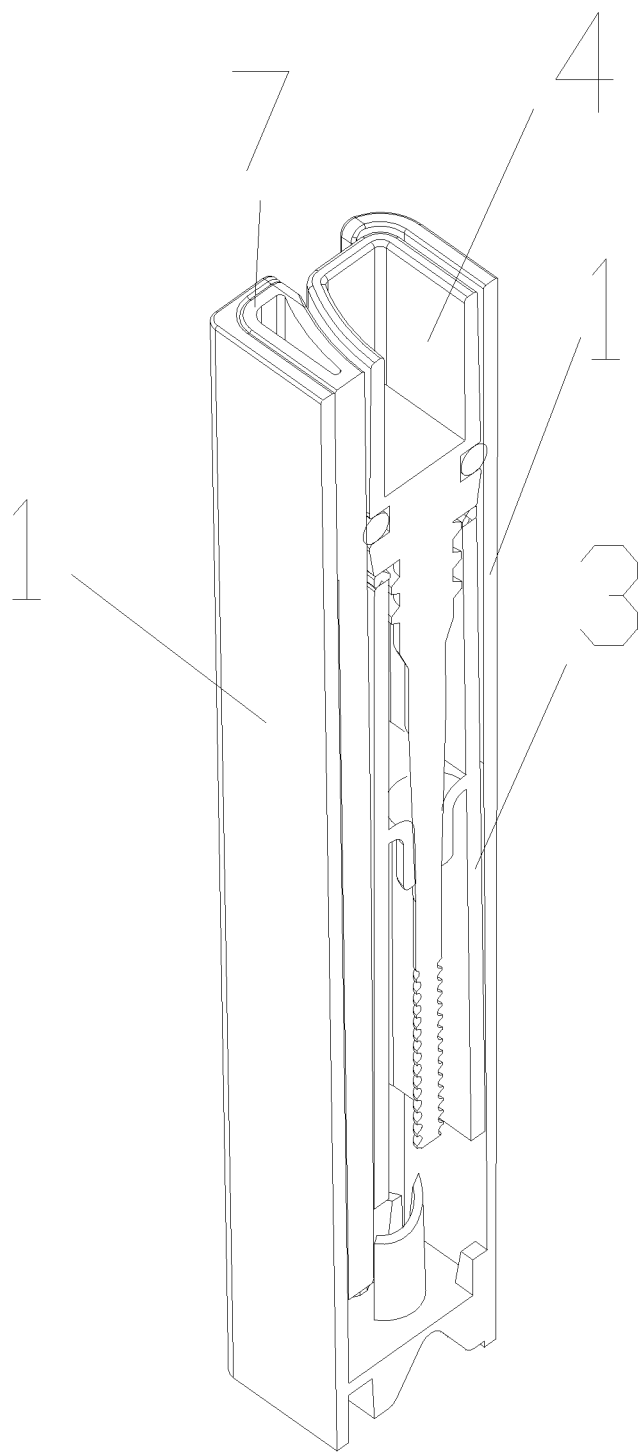
FIG. 16 is a three-dimensional structure diagram showing non-press down of a faeces collection piece, a cushion block, a collector and a test strip holder assembled into a detector according to an embodiment of the invention.
Figure 17:
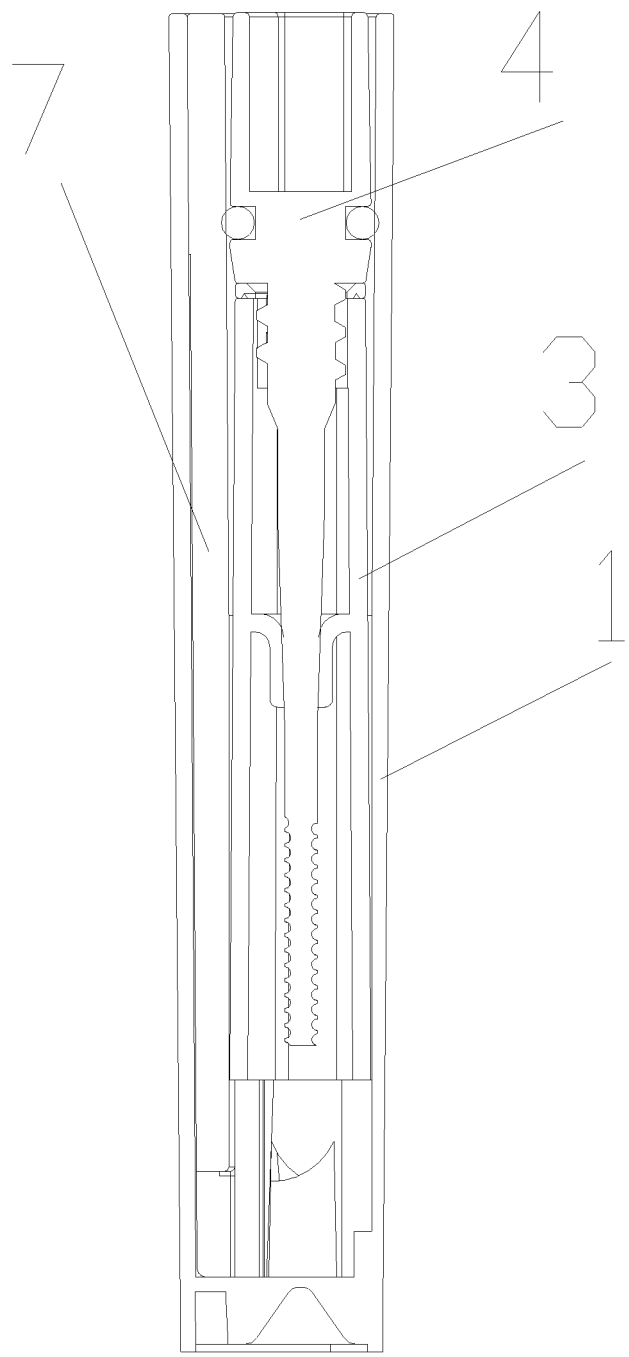
FIG. 17 is a side elevational view diagram showing non-press down of a faeces collection piece, a cushion block, a collector and a test strip holder assembled into a detector according to an embodiment of the invention.
Figure 18:
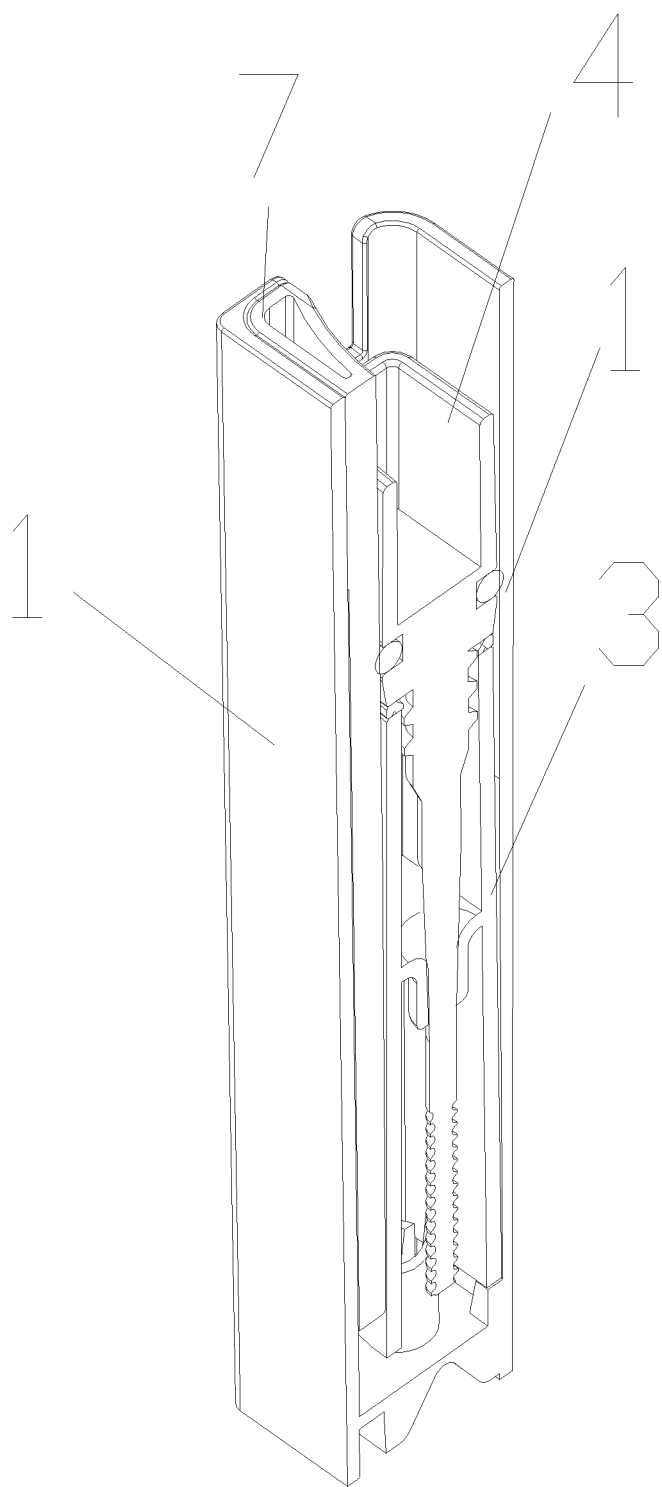
FIG. 18 is a three-dimensional structure diagram showing press down of a faeces collection piece, a cushion block, a collector and a test strip holder assembled into a detector according to an embodiment of the invention.
Figure 19:
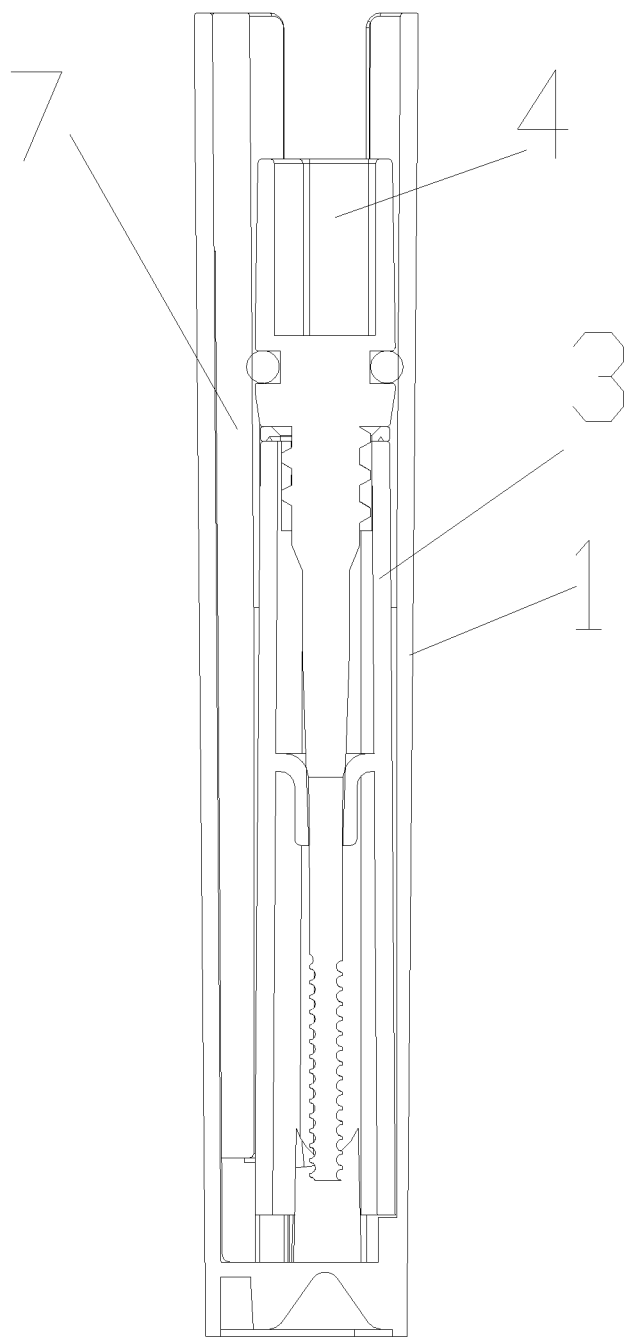
FIG. 19 is a side elevational view diagram showing press down of a faeces collection piece, a cushion block, a collector and a test strip holder assembled into a detector according to an embodiment of the invention.

A die drawing direction of the collector is inward die drawing from bottom to top, and accordingly, a lower end of the collector is larger than an upper end of the collector while a lower end of the detector is smaller than an upper end of the detector. In conjunction with the circular arc shape of the test strip holder, as shown in FIG. 14 and FIG. 16, the faeces collection piece 4, the cushion block 5, the collector 3, the test strip holder 7 and the detector 1 are smoothly assembled without interference. In addition, due to threaded fit between the faeces collection piece 4 and the cushion block 5, the directions of arc surfaces of the faeces collection piece 4 and the cushion block 5 must be consistent with the direction of an arc surface of the collector 3. That is, the combination of the faeces collection piece 4, the cushion block 5 and the collector 3 has forward and reverse properties, so the faeces collection piece 4, the cushion block 5 and the collector 3 can be smoothly assembled into the detector 1. The second outer side face 32 of the collector 3 is in a convex circular arc shape, the first outer side face 31 is a plane, an inner wall 72 of the test strip holder is in a recessed circular arc shape for instance, and the circular arc-shaped second outer side face 32 matches with the inner wall 72 of the test strip holder. Thus, as shown in FIG. 13 and FIG. 14, the collector 3, the test strip holder 7 and the detector 1 can be smoothly assembled during forward mounting.

Figure 13:
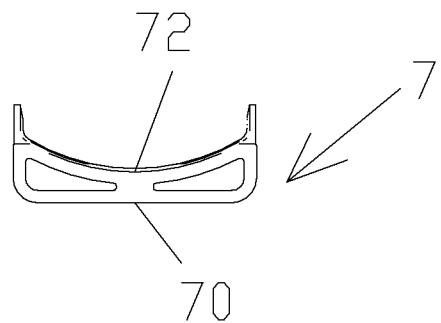
FIG. 13 is a top plan view structure diagram of a test strip holder according to an embodiment of the invention.

As shown in FIG. 13 and FIG. 15, if the components are mounted reversely, that is, if the first outer side face 31 matches with or is cling to the circular arc-shaped inner wall 72 of the test strip holder and the circular arc-shaped second outer side face 32 matches with or is cling to the inclined or straight inner wall of the detector 1, a situation that a fitting surface between a plane and an arc-shaped surface does not fit will be caused, and the faeces collection piece, the cushion block, the collector, the test strip holder and the detector are stuck due to interference. That is, during reverse mounting, the faeces collection piece, the cushion block, the collector and the test strip holder cannot be mounted into the detector. Thus, a mis-assembling prevention effect can be achieved at the beginning of mounting.

Figure 10:
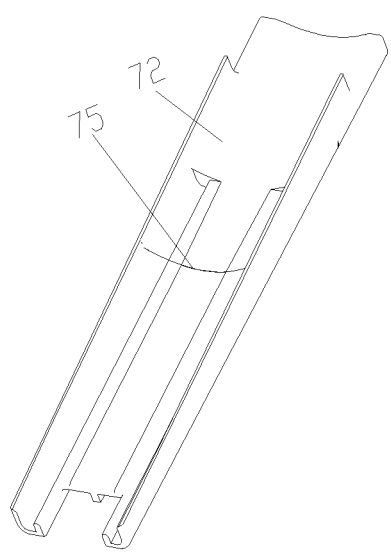
FIG. 10 shows a three-dimensional structure of a test strip holder according to an embodiment of the invention from a back view direction.
Figure 12:
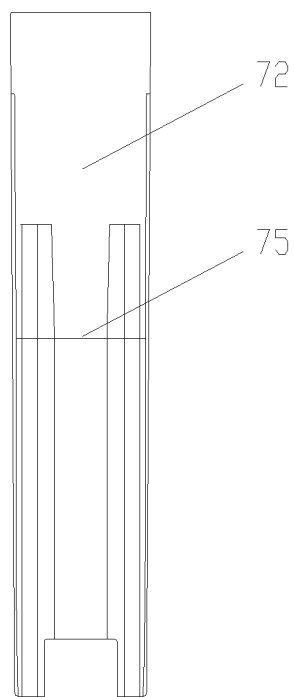
FIG. 12 is a rear elevational view plane structure diagram of a test strip holder according to an embodiment of the invention.

Furthermore, as shown in FIG. 10 and FIG. 12, a test strip holder critical line 75 (also called as an edge on the inner wall of the test strip holder) provided on the inner wall 72 of the test strip holder, the inner wall of the test strip holder is provided with a slope from the top to the test strip holder critical line 75, the slope gradually decreases, and a straight wall vertical to the bottom surface of the detector is provided below the test strip holder critical line 75. The test strip holder critical line 75 is vertical to a length direction of the test strip holder and matches with the detector critical line. The test strip holder critical line is located, for instance, at a position, ⅓ to ½ of the height of the whole test strip holder, from the top end of the test strip holder. As shown in FIG. 16, FIG. 17, FIG. 18 and FIG. 19, the straight wall structures below the critical lines of the test strip holder and the detector facilitate in-place press of the collector.

The collection and detection integrated device with a mis-assembling prevention structure of the invention is improved in terms of shapes of a faeces collection piece, a cushion block, a collector and a test strip holder of a prior faeces collection and detection device, and a symmetric regular structure of the faeces collection piece, the cushion block, the collector and the test strip holder is improved into an asymmetric irregular structure of the faeces collection piece, the cushion block, the collector and the test strip holder. A die drawing direction of the collector is inward die drawing from bottom to top, and accordingly, a lower end of the collector is larger than an upper end of the collector while a lower end of the detector is smaller than an upper end of the detector. In conjunction with the circular arc shape of a test strip holder, a mis-assembling prevention effect can be achieved at a beginning of mounting, such that the problem that the side, bonded with the bar code, of the collector is mis-assembled into the side, close to the test strip holder, of the detector is fundamentally avoided, and correct mounting of the collector bonded with the bar code and normal reading of the bar code are achieved.

The above is only a schematic specific implementation of the invention, and is not used to limit the scope of the invention. All components of the invention can be combined mutually without conflicts. Any equivalent changes and modifications made by those skilled in the art without departing from the concept and principle of the invention shall fall within the protective scope of the invention.

The invention claimed is:

1. An integrated sampling and detecting device with a misassembly prevention structure, comprising:
    a detector;
    a test strip holder, provided in the detector detachably;
    a collector, accommodated in the detector detachably; a faeces collection piece and a cushion block, configured to seal the collector detachably; and
    a piercing part, provided on a bottom surface of the detector and configured to pierce the collector,
    wherein the test strip holder and the collector are accommodated in the detector side by side, the collector is located between the test strip holder and the detector, a first outer side face of the collector is adjacent to an inner side wall of the detector, a second outer side face of the collector is adjacent to a curved wall of the test strip holder
    wherein the first outer side face of the collector is a plane and the second outer side face of the collector is a curved surface, wherein the curved wall of the test strip holder has a curved surface that is complementary to the curved surface of the second outer side face, and
    wherein the second outer side face of the collector has a recess area, wherein the recess area is provided with a rib or a needle-shaped body or a column body that projects from the recess, such that mis-bonding of a bar code to the second outer side surface is prevented.

2. The integrated sampling and detecting device with a misassembly prevention structure according to claim 1, wherein the second outer side face of the collector is a convex arc-shaped surface.

3. The integrated sampling and detecting device with a misassembly prevention structure according to claim 1, the integrated sampling and detecting device with a misassembly prevention structure further comprising: a supporting platform provided at a bottom of the detector and configured to support the collector.

4. The integrated sampling and detecting device with a misassembly prevention structure according to claim 3, wherein the piercing part is an annular body, a top surface of the annular body is a spiral surface, and the top surface of the annular body is provided with a sharp corner.

5. The integrated sampling and detecting device with a misassembly prevention structure according to claim 3, wherein the piercing part comprises a pointed cone body and an annular frustum surrounding the pointed cone body, the pointed cone body is higher than the annular frustum, an annular clearance is provided between the pointed cone body and the annular frustum, a side surface of the annular frustum is provided with an opening, the opening faces the test strip holder, and the annular clearance is communicated with the opening to form a liquid flow passage.

6. The integrated sampling and detecting device with a misassembly prevention structure according to claim 4, wherein the annular body is provided with a taper for flow guide from top to bottom.

7. The integrated sampling and detecting device with a misassembly prevention structure according to claim 3, wherein the piercing part comprises: a piercing needle and three prisms provided evenly around the piercing needle and connected with the piercing needle, the piercing needle is higher than the three prisms.

8. The integrated sampling and detecting device with a misassembly prevention structure according to claim 4, wherein the annular body comprises two pairs of semi-rings, the two semi-rings of each pair are opposite to each other; the four semi-rings are provided side by side, and the piercing part further comprises: a T-shaped prism, an outer side of each of two peripheral semi-rings which are provided at the outer sides of the four semi-rings are connected with the T-shaped prism.

9. The integrated sampling and detecting device with a misassembly prevention structure according to claim 1, wherein a side face of the test strip holder is provided with a slope decreasing from top to bottom, and an inner side of the detector is provided with a convex rib, corresponding to the slope of the test strip holder, of the detector.

10. The integrated sampling and detecting device with a misassembly prevention structure according to claim 9, wherein a trench is provided on an outer side of the test strip holder, a test strip is mounted on the trench, an inner wall of one side, adjacent to the test strip, of the detector is provided with a slope from top to bottom, three other inner walls of the detector are provided with slopes from the top to a detector critical line, a straight wall vertical to the bottom surface of the detector is provided below the detector critical line, and the detector critical line is provided on the inner wall of the detector and vertical to a length direction of the detector.

11. The integrated sampling and detecting device with a misassembly prevention structure according to claim 10, wherein a test strip holder critical line is provided on an inner side of the test strip holder, the inner side of the test strip holder is provided with a slope from the top to the test strip holder critical line, and a straight wall vertical to the bottom surface of the detector is provided below the test strip holder critical line.

12. The integrated sampling and detecting device with a misassembly prevention structure according to claim 1, wherein a lower end of the collector is larger than an upper end of the collector, and a lower end of the detector is smaller than an upper end of the detector.

13. The integrated sampling and detecting device with a misassembly prevention structure according to claim 4, wherein the annular body comprises two pairs of semi-rings, the two semi-rings of each pair are opposite to each other; the four semi-rings are provided side by side; and an outer side of each of two peripheral semi-rings which are provided at the outer sides of the four semi-rings are connected with a T-shaped prism.

14. The integrated sampling and detecting device with a misassembly prevention structure according to claim 9, wherein a trench is provided on an outer side of the test strip holder, a test strip is mounted on the trench, an inner wall of one side, adjacent to the test strip, of the detector is provided with a slope from top to bottom, three other inner walls of the detector are provided with slopes from the top to a detector critical line, the three other inner walls, below the detector critical line, of the detector are straight walls vertical to the bottom surface of the detector, and the detector critical line is provided on the inner wall of the detector and vertical to a length direction of the detector.

15. The integrated sampling and detecting device with a misassembly prevention structure according to claim 14, wherein a test strip holder critical line is provided on an inner wall of the test strip holder, the inner wall of the test strip holder is provided with a slope from a top to the test strip holder critical line, and the inner wall, below the test strip holder critical line, of the test strip holder is a straight wall vertical to the bottom surface of the detector.

* * * * *